United States Patent [19]

Schössler et al.

[11] 4,166,826

[45] Sep. 4, 1979

[54] PROCESS FOR THE PREPARATION OF 1-AMINO-8-NAPHTHOL-3,6-DISULPHONIC ACID (H-ACID)

[75] Inventors: Willi Schössler, Cologne; Rolf Pütter, Duesseldorf; Horst Behre, Odenthal, all of Fed. Rep. of Germany

[73] Assignee: Bayer Aktiengesellschaft, Leverkusen, Fed. Rep. of Germany

[21] Appl. No.: 920,032

[22] Filed: Jun. 28, 1978

[30] Foreign Application Priority Data

Jul. 16, 1977 [DE] Fed. Rep. of Germany ....... 2732266

[51] Int. Cl.$^2$ .......................................... C07C 143/66
[52] U.S. Cl. .................................................... 260/509
[58] Field of Search ......................................... 260/509

[56] References Cited

U.S. PATENT DOCUMENTS

| | | | |
|---|---|---|---|
| 1,573,056 | 2/1926 | Gubelmann et al. | 260/509 |
| 1,670,406 | 5/1928 | Gubelmann et al. | 260/509 |

OTHER PUBLICATIONS

Fiat Final Report No. 1,016, pp. 32–39.

Primary Examiner—Joseph E. Evans
Attorney, Agent, or Firm—Sprung, Felfe, Horn, Lynch & Kramer

[57] ABSTRACT

A process has been invented for the preparation of a mono-alkali metal of 1-amino-8-naphthol-3,6-disulphonic acid, comprising reacting 1-naphthylamine-3,6,8-trisulphonic acid and/or a salt thereof and/or a naphthylamine trisulphonic acid isomer mixture and/or salt thereof with an alkali metal hydroxide solution in the presence of an alcohol and/or alcoholate and in the presence of a substance which contains at least one oxygen atom bonded to a nitrogen atom, at elevated pressure and elevated temperature, and separating out the mono-alkali metal salt of 1-amino-8-naphthol-3,6-disulphonic acid by acidification. The process results in the procurement of higher yields of the desired product and in the formation of less by-products.

14 Claims, No Drawings

PROCESS FOR THE PREPARATION OF 1-AMINO-8-NAPHTHOL-3,6-DISULPHONIC ACID (H-ACID)

The present invention relates to a process for the preparation of 1-amino-8-naphthol-3,6-disulphonic acid (H-acid), in the form of the mono-alkali metal salt, from 1-naphthylamine-3,6,8-trisulphonic acid by alkaline hydrolysis under pressure.

1-Amino-8-naphthol-3,6-disulphonic acid, which is frequently designated H-acid, is an important intermediate product for the preparation of dyestuffs (see Ullmanns Enzyklopädie der Technischen Chemie (Ullmann's Encyclopaedia of Industrial Chemistry), 3rd edition, volume 12, page 621).

It is known from FIAT Final Report No. 1,016, page 32 to 39, that H-acid can be prepared as follows: naphthalene is reacted with sulphuric acid monohydrate (=100% strength $H_2SO_4$) and 65% strength oleum, a particular temperature programme being maintained and sulphuric acid monohydrate and oleum being added stepwise, to give a naphthalene-trisulphonic acid isomer mixture, which is nitrated with mixed acid. After diluting with water, driving off the nitrous gases and separating off the sulphuric acid in the form of calcium sulphate, the isomer mixture of nitronaphthalene-trisulphonic acids is reduced with iron, and dissolved iron salts are then precipitated with magnesium oxide and separated off. The acid calcium sodium salt of T-acid (1-naphthylamine-3,6,8-trisulphonic acid) is precipitated by adding rock salt and hydrochloric acid and is filtered off and washed several times. This salt of T-acid is introduced into the wash water and sodium carbonate is added. The chalk which has precipitated is then pressed out and the salt solution is concentrated. The concentrated solution of the trisodium salt of T-acid is reacted with 50% strength sodium hydroxide solution under pressure. Thereafter, first sulphuric acid and then water are added and the H-acid is finally isolated, as the monosodium salt, by filtration, washing and drying.

In this process, considerable amounts of by-products are formed during the alkaline hydrolysis under pressure of T-acid, for example 1-amino-6-naphthol-3,8-disulphonic acid, an isomer of H-acid known by the name W-acid, and 1,8-dihydroxynaphthalene-3,6-disulphonic acid, a secondary product of H-acid known by the name chromotropic acid. In general, the yield of H-acid in the process described above is only 70 to 72%, relative to T-acid employed.

According to the present invention there is provided a process for the preparation of a mono-alkali metal salt of 1-amino-8-naphthol-3,6-disulphonic acid, comprising reacting 1-naphthylamine-3,6,8-trisulphonic acid and/or a salt thereof and/or a naphthylamine trisulphonic acid isomer mixture and/or salt thereof with an alkali metal hydroxide solution in the presence of an alcohol and/or alcoholate and in the presence of a substance which contains at least one oxygen atom bonded to a nitrogen atom, at elevated pressure and elevated temperature, and separating out the mono-alkali metal salt of 1-amino-8-naphthol-3,6-disulphonic acid by acidification.

1-Naphthylamine-3,6,8-trisulphonic acid (T-acid) can be employed in the process according to the invention in the pure form and/or in the form of naphthylamine-trisulphonic acid isomer mixtures. In general, the naphthylamine-trisulphonic acid isomer mixtures contain over 65% by weight of 1-naphthylamine-3,6,8-trisulphonic acid, relative to the total amount of diazotisable substance. When naphthylaminetrisulphonic acid isomer mixtures are employed, those which contain 70 to 90% by weight of 1-naphthylamine-3,6,8-trisulphonic acid are preferably used. A naphthylamine-trisulsulphonic acid isomer mixture to be particularly preferably employed contains 75 to 85% by weight of 1-naphthylamine-3,6,8-trisulphonic acid, 5 to 15% by weight of 1-naphthylamine-3,5,7-trisulphonic acid, 1 to 10% by weight of 1-naphthylamine-4,6,8-trisulphonic acid, 0.5 to 5% by weight of 1-naphthylamine-2,5,7-trisulphonic acid, 0.1 to 2% by weight of 2-naphthylamine-3,5,7-trisulphonic acid, 0.1 to 2% by weight of 2-naphthylamine-4,6,8-trisulphonic acid and 0.1 to 2% by weight of 2-naphthylamine-3,6,8-trisulphonic acid.

In addition to the naphthylamine-trisulphonic acids, naphthylamine-trisulphonic acid isomer mixtures can also contain further products. Such products can be, in particular, by-products, decomposition products or unreacted intermediate products from the preparation stages of naphthylamine-trisulphonic acid, for example naphthalene-di-, -tri- and -tetrasulphonic acids, nitronaphthalene-mono-, -di and -tri-sulphonic acids, naphthylamine-mono- and -di-sulphonic acids, for example 1-naphthylamine-3,6- and 5,7-disulphonic acid, and furthermore dinaphthylsulphone-sulphonic acids and their amino and nitro derivatives, as well as oxidation products of naphthalene and/or of the naphthalene-sulphonic acids which can be formed during the sulphonation and/or the nitration.

1-Naphthylamine-3,5,8-trisulphonic acid or the naphthylamine-trisulphonic acid isomer mixtures can be employed in the free form, in the form of neutral salts or in the form of acid salts. Mixtures which contain the free acids and salts can also be used. If all or some of the 1-naphthylamine-3,6,8-trisulphonic acid or naphthylamine-trisulphonic acid isomer mixtures are present as the salts, the alkali metal salts and alkaline earth metal salts, in particular the sodium salts and potassium salts, are preferred.

1-Naphthylamine-3,6,8-trisulphonic acid, or salts of this acid, suitable for use in the process according to the invention can be obtained by trisulphonating naphthalene, nitrating the mixture formed, reducing the nitro-Naphthalene-Trisulphonic acid mixture then present, precipitating the acid calcium sodium salt of T-acid, adding sodium carbonate to a solution of this salt, pressing out the chalk which has precipitated and concentrating the salt solution. These reactions can be carried out by the initially described procedure according to FIAT Final Report No. 1016 or in any other desired manner.

A naphthylamine-trisulphonic acid isomer mixture suitable for use in the process according to the invention can be obtained in a similar manner if the reaction sequence is interrupted after the reduction of the nitro-naphthalene-trisulphonic acid mixture has ended.

The 1-naphthylamine-3,6,8-trisulphonic acid and/or salts thereof and/or the naphthylamine-trisulphonic acid isomer mixture and/or salts thereof can be employed, for example, in the solid form or in the form of an aqueous solution having a content of, for example, 20 to 50% by weight, preferably 30 to 40% by weight, calculated as the free acid with the molecular weight 383.

Alkali metal hydroxide solutions which can be used for the process according to the invention are, in particular, aqueous potassium hydroxide solution or sodium hydroxide solution. Compared with sodium hydroxide solution, using potassium hydroxide solution leads to better yields, but in general sodium hydroxide solution is less expensive. 2.5 to 12 mols of alkali metal hydroxide, for example, can be employed per mol of diazotisable substance (calculated with a molecular weight of 383=T-acid). 6 to 9 mols of alkali metal hydroxide are particularly preferably used per mol of diazotisable substance. The concentration of alkali metal hydroxide in the reaction mixture can be, for example, 10 to 50% by weight (relative to the sum of alkali metal hydroxide plus water plus alcohol). This concentration is preferably 25 to 35%.

It is an essential aspect of the process according to the invention that the process is carried out in the presence of an alcohol and/or alcoholate and in the presence of a substance which contain at least one oxygen atom bonded to a nitrogen atom. The alcohol to be added can be introduced into the reaction mixture, for example, in the pure form, mixed with water or in the form of an alcoholate, for example in the form of an alkali metal alcoholate. Suitable alcohols are those alcoholic compounds which under the reaction conditions are water-miscible and do not enter into undesired side reactions, or enter into undesired side reactions only to a slight extent, with the strong alkali. In this case, the formation of an alcoholate is not an undesired side reaction. Aliphatic alcohols with, for example, 1-6 carbon atoms are preferably used. Examples of alcohols which can be used are primary, secondary and tertiary monohydric and polyhydric alcohols (particularly alkanols, alkanediols and alkane triols, all or some of the hydroxyl groups of which can also be etherified. Said etherified hydroxyl groups are preferably derived from $C_1$–$C_6$-alkanols. Examples of monohydric alcohols which can be used are: methanol, ethanol, n-propanol, 2-propanol, n-butanol, iso-butanol and tert.-butanol. Examples of polyhydric alcohols which can be used are: ethylene glycol, propanediols, butanediols glycerol, butanetriols, monoglymes and diglymes. It is also possible, of course, to use mixtures of alcohols. Methanol is particularly preferably employed.

The amount of alcohol or alcoholate to be employed can be chosen, for example, such that 10 to 80% by weight, preferably 25 to 60% by weight, of alcohol or alcoholate, relative to the sum of water plus alcohol, are present.

The presence of a substance which contains at least one oxygen atom bonded to a nitrogen atom can be achieved, for example, by adding a nitrogen/oxygen acid or a derivative of a nitrogen/oxygen acid to the reaction mixture. For example, nitric acid, nitrous acid, a nitrogen oxide, a nitrate, nitrite, nitro compound or nitroso compound can be added to the reaction mixture. Examples of nitrogen oxides which can be used are $N_2O_5$, $N_2O_4$, $N_2O_3$, $NO_2$ and $NO$, preferably $N_2O_5$ and $N_2O_4$, or $NO_2$. Examples of nitrates which can be used are alkali metal nitrates, ammonium nitrates, alkaline earth metal nitrates and other metal nitrates, including heavy metal nitrates. Alkali metal nitrates, in particular sodium nitrate or potassium nitrate, are preferably employed. Examples of nitrites which can be used are alkali metal nitrites, in particular sodium nitrite. Examples of nitro compounds which can be used are aromatic and aliphatic nitro compounds, such as nitrobenzenes, nitronaphthalenes, nitrobenzenesulphonic acid, nitronaphthalene-mono-, -di- and -tri-sulphonic acids, nitromethane, nitroethane and nitropropane. Examples of nitroso compounds which can be used are nitrosobenzenes.

Those compounds which themselves are soluble, or which give secondary products which are soluble, under the conditions for the precipitation of the mono-alkali metal salt of H-acid are preferably employed, such as nitrogen/oxygen acids nitrogen oxides, nitrates, nitrites and nitro compounds which are soluble in an acid medium. Thus, no particular provisions have to be made for separation of these additives since these, or their secondary products are then contained in the effluent after separating off the H-acid as the mono-alkali metal salt.

The process according to the invention is particularly preferably carried out in the presence of sodium nitrate or potassium nitrate.

The additives described above can be introduced into the reaction mixture during the process according to the invention in the pure form or in the form of a solution, preferably as a solution in water, aqueous alkali or alcohol. It is also possible, of course, to employ 2 or more of the additives mentioned.

In general, it suffices for the substances which contain at least one oxygen atom bonded to a nitrogen atom to be present in the reaction mixture in low amounts. It is possible, for example, to introduce into the reaction mixture an amount of these substances such that, relative to 1 mol of 1-naphthylamine-3,6,8-trisulphonic acid employed or 1 mol of naphthylamine-trisulphonic acid isomer mixture or 1 mol of salts of these acids, 0.005 to 1 mol of these substances are present. These substances are preferably present in an amount of 0.01 to 0.5 mol, in particular in an amount of 0.01 to 0.1 mol (relativity as above).

The process according to the invention can be carried out, for example, at temperatures from 150° to 250° C., preferably at 180° to 220° C., in a closed vessel. The pressure thereby set up is generally completely sufficient to carry out the process according to the invention in a satisfactory manner. It is also possible, of course, to carry out the process according to the invention at other pressures than those which are automatically set up in closed vessels. For example, pressures in the range from 5 to 100 bars are possible for the process according to the invention.

The reaction time largely depends on the reaction temperature and the alkali metal hydroxide concentration. It is shorter at relatively high reaction temperatures and at relatively high alkali metal hydroxide concentrations and longer at relatively low reaction temperatures and relatively low alkali metal concentrations, and in general is 10 minutes to 10 hours. For example, good results are obtained with a reaction time of 45–60 minutes at a reaction temperature of about 200° C. and an alkali metal hydroxide concentration of 30% by weight.

The substances to be employed in the process according to the invention are most appropriately introduced into the reaction vessel at a temperature such that after the heat of mixing and, if appropriate, the heat of neutralisation has been released, the temperature is the desired reaction temperature. The substances to be introduced can also be brought together at relatively low temperatures and heated to the desired reaction temperature in the reaction vessel.

After the reaction has ended and before the H-acid is separated out as the mono-alkali metal salt, it is advantageous to cool the reaction mixture and/or to dilute it with water. The mixture can be cooled, for example, to temperatures in the range from 20° to 150° C., preferably to temperatures in the range from 80° to 120° C. The amount of water to be appropriately added depends on the reaction conditions, for example the nature of the alkali metal hydroxide and its amount and concentration, and the amount of alcohol which may also be present. It is advantageous to choose the amount of water such that the alkali metal sulphite formed during the reaction is dissolved or remains dissolved.

The H-acid is separated out as the mono-alkali metal salt by acidifying the reaction mixture with mineral acids.

Sulphuric acid is preferably used for this. An amount of mineral acid is added such that the sparingly soluble mono-alkali metal salt of H-acid forms. By appropriately choosing the concentration of the mineral acid and/or by adding water before and/or during the addition of the mineral acid, it is appropriately ensured that the organic salt which forms, for example sodium sulphate or potassium sulphate, does not precipitate. Good results are obtained, for example, if, in order to separate out the H-acid as the mono-alkali metal salt, the pH is adjusted to a value in the range from 0 to 4, preferably 0.5 to 2.5, and 0.1 to 5 times, preferably 0.5 to 2 times, the amount of water is introduced, relative to the weight of the mixture present in the hydrolysis under pressure, by diluting with water and/or by appropriately choosing the concentration of the mineral acid. The mono-alkali metal salt of H-acid can be separated off in the customary manner, for example by filtration. It is advantageous to adjust the temperature to less than 80° C. by cooling, for example by evaporative cooling, before separating off the mono-alkali metal salt of H-acid, and to carry out the separation at a temperature of less than 80° C. The separation is preferably carried out at a temperature in the range from 20° to 60° C.

In order to completely remove sulphur dioxide, after adjusting the precipitation conditions and before separating off the mono-alkali metal salt of H-acid it is advantageous for the acidified and diluted mixture to be boiled under reflux, or to be kept under a vacuum, for some time, for example 0.5 to 2 hours, or for the sulphur dioxide to be blown out with an inert gas, for example nitrogen.

The mono-alkali metal salt of H-acid present after the separation is usually washed with water, and is dried, for example in vacuo.

After the reaction, the alcohol can be separated off during the working up of the reaction mixture at various stages. It is possible to separate off the alcohol from the alkaline, neutral or acid solution, before or after separating off the H-acid as the mono-alkali metal salt. The alcohol is preferably separated off from the alkaline or neutral solution and by distillation. It is particularly preferable to distil off the alcohol directly from the reaction mixture, preferably after cooling and/or diluting with water, over a column. If low-boiling alcohols are used, for example methanol, it can suffice to start the distillation by letting down the pressure, without supplying external heat. If the alcohol used demixes out of the reaction mixture at temperatures which are lower than the reaction temperature, it is also possible to separate off the alcohol by phase separation after cooling the reaction mixture.

The alcohol separated off is preferably reused in the process according to the invention. It is then only necessary to replace the portions of alcohol lost, appropriately during the alkaline hydrolysis under pressure and/or during working up.

Compared with known processes for the preparation of 1-amino-8-naphthol-3,6-disulphonic acid (H-acid) as a mono-alkali metal salt, the process according to the invention has the advantage that higher yields can be achieved and the formation of by-products, in particular the formation of 1-amino-6-naphthol-3,8-disulphonic acid (W-acid) and the formation of 1,8-dihydroxynaphthalene-3,6-disulphonic acid (chromotropic acid) is considerably decreased. The decreased content of W-acid, which is sparingly soluble in acid solution, additionally makes it possible to isolate the mono-alkali metal salt of H-acid in a particularly pure form without intensive washing, which is associated with yield losses.

EXAMPLES

EXAMPLE 1

580 g of a naphthylaminetrisulphonic acid mixture in the form of the trisodium salts (content: 11.9 g of total nitrite/100 g and 52.8% by weight of T-acid MW 383; a total of 69 g of nitrite and 0.80 mol of T-acid) of the following composition:

1-Naphthylamine-3,6,8-trisulphonic acid—80.0%
1-Naphthylamine-3,5,7-trisulphonic acid—8.5%
1-Naphthylamine-4,6,8-trisulphonic acid—4.0%
1-Naphthylamine-2,5,7-trisulphonic acid—3.0%
2-Naphthylamine-3,5,7-trisulphonic acid—1.2%
2-Naphthylamine-4,6,8-trisulphonic acid—0.7% and
2-Naphthylamine-3,6,8-trisulphonic acid—0.5%

(The contents in % are in each case relative to diazotisable substance), which additionally contains 0.3% by weight of disodium 1-naphthylamine-3,6-disulphonate, 1.3% by weight of trisodium naphthalene-1,3,6-trisulphonate, 0.6% by weight of trisodium 1-nitronaphthalene-3,6,8-trisulphonate, 4.6% by weight of water and amounts, which cannot be determined quantitatively, of amino and nitro derivatives of dinaphthylsulphone-sulphonic acids and of oxidation products of naphthalene and of naphthalene-trisulphonic acids, 325 g of water, 310 g of methanol and (a) 8.5 g (0.1 mol) of sodium nitrate, (b) 4.2 g (0.05 mol) of sodium nitrate, (c) 0.8 g (0.01 mol) of sodium nitrate or (d) 6.9 g (0.1 mol) of sodium nitrite are initially introduced into a 2.7 l nickel autoclave and the mixture is heated to 210° C. 474 g of 70% strength by weight sodium hydroxide solution (8.3 mols of NaOH) are heated to 210° C. in a 1.3 l steel autoclave and are quantitatively forced, using nitrogen, into the 2.7 l autoclave, whereupon a 30% strength by weight sodium hydroxide solution, relative to the sum of water plus methanol, is formed. A temperature of 220° C. is thereby set up. The reaction mixture is kept at 220° C. for 20 minutes, cooled as rapidly as possible and diluted with about 500 g of water, the methanol is distilled off over a column and the reaction mixture which has been freed from methanol is analysed quantitatively by high pressure liquid chromatography.

Table 1 shows the test results obtained:

Table 1

| Example | Product distribution in the reaction mixture which has been freed from methanol, in mol %, relative to T-acid employed | |
|---|---|---|
| | H-acid MW 319 | 1-Naphthylamine-3,6-disulphonic acid MW 303 |
| 1 a | 82.4 | 1.8 |

Table 1-continued

5. Reaction time give the results summarised in Table 3.

Table 3

| | Reaction conditions | | | | | Quality of the isolated solid product + | | | | | |
| --- | --- | --- | --- | --- | --- | --- | --- | --- | --- | --- | --- |
| Ex. | Molar ratio of NaOH to T-acid isomer mixture (MW 383) mol % | NaOH concentration, relative to water plus methanol % by weight | Weight ratio of water to methanol | Sodium nitrate addition, relative to naphthylamine-sulphonic acid mixture employed mol % | Time minute | Yield relative to T-acid employed mol % | H-acid MW 319 % by weight | 1-Naphthylamine-3,6-disulphonic acid MW 303 % by weight | Chromotropic acid MW 320 % by weight | T-acid MW 383 % by weight | $H_2O$ % by weight | $Na_2SO_4$ % by weight |
| 2 a | 8.1:1 | 30 | 3:2 | 10.0 | 60 | 79.5 | 79.9 | 0.1 | 0.4 | — | 12.1 | 2.4 |
| 2 b | 7.5:1 | 30 | 3:2 | 10.0 | 51 | 79 | 81.1 | 0.05 | 0.3 | — | 12.0 | 0.7 |
| 2 c | 8.3:1 | 30 | 3:2 | 7.5 | 45 | 81 | 81.3 | 0.05 | 0.4 | 0.1 | 11.9 | 0.7 |
| 2 d | 7.5:1 | 30 | 3:2 | 7.5 | 50 | 80 | 81.3 | 0.1 | 0.3 | — | 12.1 | 0.6 |
| 2 e | 7.5:1 | 25 | 3:2 | 7.5 | 70 | 80 | 81.1 | — | — | — | 12.6 | 0.6 |
| 2 f | 7.3:1 | 25 | 2:1 | 7.5 | 85 | 77.5 | 80.6 | 0.05 | 0.5 | — | 12.9 | 0.4 |
| 2 g | 7.5:1 | 30 | 3:2 | 5.0 | 52 | 80 | 81.9 | 0.2 | 0.3 | — | 11.7 | 0.5 |
| 2 h | 7.1:1 | 30 | 3:2 | 5.0 | 55 | 79 | 79.8 | 0.15 | 0.6 | — | 12.0 | 1.9 |

+W-acid (MW 319) could not be detected in any of the products. The contents of acids indicated are calculated relative to the free acids. In fact, they are present in the form of the salts indicated in Table 2.

| | Product distribution in the reaction mixture which has been freed from methanol, in mol %, relative to T-acid employed | |
| --- | --- | --- |
| Example | H-acid MW 319 | 1-Naphthylamine-3,6-disulphonic acid MW 303 |
| 1 b | 81.6 | 2.2 |
| 1 c | 79.0 | 4.7 |
| 1 d | 78.7 | 5.3 |

The reaction mixtures which have been freed from methanol are acidified with about 1,000 g of 50% strength by weight sulphuric acid, the pH being controlled at 1 to 1.5, heated under reflux for one hour in order to completely remove sulphur dioxide, cooled to 40° C., with evaporative cooling, and kept at 40° C. for two hours. The product is filtered off at 40° C., washed with a total of 500 g of water and dried at 80° C. in vacuo. The yields and the quality of the H-acid, which was determined by high pressure liquid chromatography, are given in Table 2.

Table 2

| | Quality of the isolated solid product+ | | | | | | |
| --- | --- | --- | --- | --- | --- | --- | --- |
| Example | Yield relative to T-acid employed mol % | H-acid MW 319 % by weight | 1-Naphthylamine 3,6-disulphonic acid MW 303 % by weight | W-acid MW 319 % by weight | Chromotropic acid MW 320 % by weight | T-acid MW 383 % by weight | Water % by weight | Sodium sulphate % by weight |
| 1 a | 80 | 80.0 | 0.1 | — | 0.5 | — | 11,8 | 1.7 |
| 1 b | 79.5 | 81.0 | 0.2 | — | 0.6 | — | 11.8 | 0.9 |
| 1 c | 78 | 81.1 | 0.5 | — | 0.5 | — | 11.5 | 0.7 |
| 1 d | 77 | 81.3 | 0.6 | — | 0.6 | — | 11.9 | — |

+The contents of acids indicated are calculated with respect to the free acids. In fact, they are present as the monosodium salts (H-acid, W-acid and 1-naphthylamine-3,6-disulphonic acid) or disodium salts (chromotropic acid and T-acid).

EXAMPLES 2a–2h

Further reactions carried out as in Example 1, but without analysing the reaction mixture which has been freed from methanol, at 200° C., varying the reaction parameters:
1. Molar ratio of NaOH to the trisodium salt of the T-acid isomer mixture
2. NaOH concentration
3. Weight ratio of water to methanol
4. Amount of sodium nitrate added EXAMPLES 3a–3e 580 g of the naphthylaminetrisulphonic acid mixture indicated in Example 1, 275 g of water, 280 g of methanol and the amount of further additive indicated in the table which follows are initially introduced into a 2.7 l nickel autoclave and heated to 190° C. 430 g of 70% strength sodium hydroxide solution (7.5 mols of NaOH) are heated to 190° C. in a 1.3 l steel autoclave and forced quantitatively, using nitrogen, into the 2.7 l autoclave, whereupon a 30% strength by weight sodium hydroxide solution, relative to water plus methanol, forms. A temperature of 200° C. is thereby set up. The reaction mixture is kept at 200° C. for 50 minutes, cooled as rapidly as possible and diluted with about 500 g of water, the methanol is distilled off over a column and the reaction mixture which has been freed from methanol is analysed quantitatively by high pressure liquid chromatography.

Table 4 shows the test results obtained:

Table 4

| Example | Further additive in mol %, relative to naphthylamine-trisulphonic acid mixture employed | In the form of | Product distribution in the reaction mixture, which has been freed from methanol, in mol %, relative to T-acid employed | |
|---|---|---|---|---|
| | | | H-acid MW 319 | 1-Naphthylamine-3,6-disulphonic acid MW 303 |
| 3 a | 5.0 | Na 2-nitro-benzene-sulphonate | 78.2 | 6.3 |
| 3 b | 5.0 | The trisodium salt of nitro-T-acid | 79.4 | 5.4 |
| 3 c | 5.0 | Nitrobenzene | 80.5 | 4.0 |
| 3 d | 5.0 | Copper nitrate | 83.9 | 0.8 |
| 3 e | 7.5 | Sodium nitrate | 84.3 | 0.5 |

EXAMPLE 4

450 g (1 mol) of the trisodium salt of T-acid (content: 15.3 g of nitrite/100 g and 85.1% by weight of T-acid MW 383; a total of 69 g of nitrite), 325 g of water, 310 g of methanol and 8.5 g (0.1 mol) of sodium nitrate are initially introduced into a 2.7 l nickel autoclave and heated to 200° C. 474 g of 70% strength by weight sodium hydroxide solution (8.3 mols of NaOH) are heated to 215° C. in a 1.3 l steel autoclave and are forced quantitatively, using nitrogen, into the 2.7 l autoclave, whereupon a 30% strength by weight sodium hydroxide solution, relative to the sum of water plus methanol, forms. A temperature of 220° C. is thereby set up. The reaction mixture is kept at 220° C. for 15 minutes, cooled as rapidly as possible and diluted with about 500 g of water and the methanol is distilled off over a column. The hot reaction solution is allowed to run into a hot mixture of 325 ml of 96% strength sulphuric acid and 1.5 l of water. The resulting H-acid suspension is boiled under reflux for one hour, in order to remove sulphur dioxide, cooled to 40° to 45° C. and kept at 40° to 45° C. for one hour. The product is filtered off at 40° C., washed with a total of 500 g of water and dried at 80° C. in vacuo. The yield is 82% of theory.

Content [% by weight]:

| | |
|---|---|
| H-acid (MW 319) | 80.4 |
| 1-Naphthylamine-3,6-disulphonic acid (MW 303) | — |
| W-acid (MW 319) | — |
| Chromotropic acid (MW 320) | 0.5 |
| T-acid (MW 383) | — |
| $H_2O$ | 12.3 |
| $Na_2SO_4$ | 1.2 |

The contents of the acids indicated are calculated relative to the free acids. In fact the salts mentioned in Example 1 are present.

EXAMPLE 5

5.9 kg of a naphthylamine-trisulphonic acid mixture in the form of the trisodium salts (content: 11.7 g of total nitrite/100 g and 53.9% by weight of T-acid of molecular weight 383, a total of 0.69 kg of nitrite and 8.3 mols of T-acid) of the following composition:

1-Naphthylamine-3,6,8-trisulphonic acid—83.0%,
1-Naphthylamine-3,5,7-trisulphonic acid—7.3%
1-Naphthylamine,4,6,8-trisulphonic acid—3.4%
1-Naphthylamine-2,5,7-trisulphonic acid—3.2%
2-Naphthylamine-3,5,7-trisulphonic acid—0.8%
2-Naphthylamine-4,6,8-trisulphonic acid—0.3% and
2-Naphthylamine-3,6,8-trisulphonic acid—0.5%

(The contents in percent are in each case relative to diazotisable substance), which additionally contains 0.2% by weight of disodium 1-naphthylamine-3,6-disulphonate, 1.1% by weight of trisodium naphthalene-1,3,6-trisulphonate, 5.4% by weight of water and amounts, which cannot be determined quantitatively, of amino and nitro derivatives of dinaphthylsulphone-sulphonic acid and of oxidation products of naphthalene and of naphthalene-trisulphonic acids, and 2.8 kg of water, 2.8 kg of methanol and 64 g (0.75 mol) of sodium nitrate are heated to 180° C. in a 20 l nickel autoclave. 4.3 kg of 70% strength by weight sodium hydroxide solution 75 mols of NaOH), having a temperature of 180° C., are pumped in in the course of about 5 minutes, whilst blanketing with nitrogen, a temperature of 200° C. being set up. The reaction mixture is kept at 200° C. for 55 minutes and let down in a 25 l stainless steel kettle, into which 10 l of cold water have been initially introduced. The methanol is distilled off and the dilute H-acid isomer mixture solution is forced, using nitrogen and in the course of 40 to 60 minutes, into a precipitation vessel made of glass, into which about 4 kg of water (or the wash water from the previous batch) have been initially introduced. The pH is kept at 1 to 1.5 by simultaneously adding about 5.2 kg of 100% strength sulphuric acid and the reaction mixture is brought to the boil. The hot, acid H-acid suspension is freed from residual sulphur dioxide by applying a vacuum, cooled to 40° C. in the course of one hour, kept at 40° C. for one hour and filtered. The product is washed with a total of 5.4 kg of water and dried at 80° C. in vacuo. The yield is 82%, relative to T-acid. The qualities of the product, determined by high pressure liquid chromatography, are listed in Table 5.

EXAMPLE 6

A reaction carried out as in Example 5, but in which the reaction temperature is 190° C. and the reaction time is 100 minutes, gives a yield of 83%, relative to T-acid. The quality of the product, determined by high pressure liquid chromatography, is given in Table 5.

Table 5

| | Quality of the isolated solid product+ | | | | |
|---|---|---|---|---|---|
| | H-acid MW 319 | 1-Naphthylamine-3,6-disulphonic acid MW 303 | W-acid MW 319 | Chromotropic acid MW 320 | T-acid MW 383 |
| Example | % by weight | % by weight | % by weight | % by weight | % by weight |
| 5 | 81.3 | 0.1 | — | 0.7 | 0.3 |
| 6 | 80.8 | 0.1 | — | 1.0 | 0.2 |

+To make up to 100%, virtually one sodium sulphate and water are still present. The contents of acids indicated are calculated relative to the free acids. In fact, these are present in the form of the salts indicated in Example 2.

EXAMPLE 7 (COMPARISON EXAMPLE)

580 g of a naphthylaminetrisulphonic acid mixture in the form of the trisodium salts (content: 11.9 g of total nitrite/100 g and 52.8% by weight of T-acid MW 383; a total of 69 g of nitrite and 0.80 mol of T-acid) of the following composition:

1-Naphthylamine-3,6,8-trisulphonic acid—80.0%
1-Naphthylamine-3,5,7-trisulphonic acid—8.5%
1-Naphthylamine-4,6,8-trisulphonic acid—4.0%
1-Naphthylamine-2,5,7-trisulphonic acid—3.0%
2-Naphthylamine-3,5,7-trisulphonic acid—1.2%
2-Naphthylamine-4,6,8-trisulphonic acid—0.7% and
2-Naphthylamine-3,6,8-trisulphonic acid—0.5%

(The contents in % are in each case relative to diazotisable substance), which additionally contains 0.3% by weight of disodium 1-naphthylamine-3,6-disulphonate, 1.3% by weight of trisodium naphthalene-1,3,6-trisulphonate, 0.6% by weight of trisodium 1-nitronaphthalene-3,6,8-trisulphonate, 4.6% by weight of water and amounts, which cannot be determined quantitatively, of amino and nitro derivatives of dinaphthyl-sulphone-sulphonic acid and of oxidation products of naphthalene and of naphthalene-trisulphonic acids, and 400 g of water are initially introduced into a 2.7 liter nickel autoclave and heated to 180° C. 600 g of 50% strength by weight sodium hydroxide solution (7.5 mols of NaOH) are heated to 185° C. in a 1.3 liter steel autoclave and are forced, using nitrogen, into the 2.7 liter autoclave, whereupon a 30% strength by weight sodium hydroxide solution, relative to the total water, forms. A temperature of 200° C. is thereby set up. The reaction mixture is kept at 200° C. for 45 minutes, cooled to 100° C. as rapidly as possible and diluted with 500 g of water. The hot reaction solution is acidified with about 1,000 g of 50% strength by weight sulphuric acid, the pH being controlled (pH 1 to 1.5), heated under reflux for one hour in order to completely remove sulphur dioxide, cooled to 40° C., with evaporative cooling, and kept at 40° C. for 2 hours. The product is filtered off at 40° C., washed with a total of 500 g of water and dried at 80° C. in vacuo.

The yield is 58%, relative to T-acid isomer mixture, or 72%, relative to T-acid. The H-acid quality was determined by high pressure liquid chromatography to be as follows.

Monosodium salt of H-acid—88.2%
Monosodium 1-naphthylamine-3,6-disulphonate—0.1–0.2%
Monosodium salt of W-acid—0.1–0.2%
Disodiu salt of chromotropic acid—1.1–1.2%
Disodium salt of T-acid—0.1–0.2%
Water—9.0%
Sodium sulphate—0.5%

The isolated product does not contain reaction products from the isomeric naphthylaminetrisulphonic acids.

EXAMPLE 8 (COMPARISON EXAMPLE)

A reaction carried out as in Example 7, but using the pure trisodium salt of T-acid gives a yield of 73%, but an increased content of W-acid and T-acid.
Content:
Monosodium salt of H-acid—88.6%
Monosodium 1-naphthylamine-3,6-disulphonate—0.2%
Monosodium salt of W-acid—2.0%
Disodium salt of chromotropic acid—1.4%
Disodium salt of T-acid—0.6%
Water—6.8%
Sodium sulphate—0.6%

What is claimed is:

1. A process for the preparation of a mono-alkali metal salt of 1-amino-8-naphthol-3,6-disulphonic acid which comprises reacting 1-naphthylamine-3,6,8-trisulphonic acid and/or a salt thereof and/or a naphthylamine-trisulphonic acid isomer mixture and/or salt thereof with an alkali metal hydroxide solution in the presence of an aliphatic having from 1 to 6 carbon atoms and/or alcoholate thereof and in the presence of a substance which contains at least one oxygen atom bonded to a nitrogen atom, at elevated pressure and elevated temperature, and separating out the mono-alkali metal salt of 1-amino-8-naphthol-3,6-disulphonic acid by acidification.

2. A process according to claim 1 wherein the naphthylamine-trisulphonic acid isomer mixture contains from 70 to 90% by weight of the 1-naphthylamine-3,6,8-trisulphonic acid.

3. A process according to claim 1 or 2 wherein the alcohol is methanol.

4. A process according to claim 1 wherein 10 to 80% by weight of alcohol and/or alcoholate, relative to the sum of water plus alcohol, is present in the reaction mixture.

5. A process according to claim 1 wherein a nitrogen/oxygen acid or a derivative of a nitrogen/oxygen acid is present in the reaction mixture.

6. A process according to claim 1 wherein nitric acid, nitrous acid, a nitrogen oxide, a nitrate, nitrite, nitro compound or nitroso compound is present in the reaction mixture.

7. A process according to claim 6 wherein the nitrate is sodium nitrate or potassium nitrate.

8. A process according to claim 1 wherein from 0.005 to 1 mol of the substance which contains at least one oxygen atom bonded to a nitrogen atom is introduced into the reaction mixture per mol of 1-naphthylamine-3,6,8-trisulphonic acid, or per mol of naphthylamine-trisulphonic acid isomer mixture, or per mol of the salt of these acids.

9. A process according to claim 1 wherein the reaction temperature is from 150° to 250° C.

10. A process according to claim 1 wherein the reaction is carried out in a closed vessel.

11. A process according to claim 1 wherein the reaction is carried out under a pressure of from 5 to 100 bars.

12. A process according to claim 1 wherein acidification is carried out by the addition of the sulphuric acid.

13. A process according to claim 1 wherein, after the reaction is complete, the alcohol is separated off from the alkaline or neutral solution by distillation.

14. A process according to claim 13 wherein the alcohol which is separated off is reused.

* * * * *

UNITED STATES PATENT AND TRADEMARK OFFICE
CERTIFICATE OF CORRECTION

PATENT NO. : 4,166,826
DATED : September 4, 1979
INVENTOR(S) : Willi Schossler, et al.

It is certified that error appears in the above–identified patent and that said Letters Patent are hereby corrected as shown below:

In the abstract, column 1, line 2, insert --salt-- after "metal".
Column 2, line 3, "naphthylaminetrisulphonic" should be --naphthylamine-trisulphonic--.
Column 2, line 32, "3,5,8" should be --3,6,8--.
Column 5, line 21, "organic" should be --inorganic--.
Column 6, line 10, "/" should be --1--.
Column 8, Table, 2, Example 1a under "Water" "11,8" should be --11.9--.
Column 12, line 15, insert --alcohol-- after "aliphatic".

Signed and Sealed this

Eighteenth Day of December 1979

[SEAL]

Attest:

Attesting Officer

SIDNEY A. DIAMOND

Commissioner of Patents and Trademarks